United States Patent [19]

Plummer

[11] Patent Number: 4,758,590
[45] Date of Patent: Jul. 19, 1988

[54] METHOD FOR CONTROL OF SOIL-BORNE INSECTS

[75] Inventor: Ernest L. Plummer, Yardley, Pa.

[73] Assignee: FMC Corporation, Philadelphia, Pa.

[21] Appl. No.: 589,622

[22] Filed: Mar. 14, 1984

[51] Int. Cl.$^4$ ............................................. A01N 53/00
[52] U.S. Cl. ..................................................... 514/531
[58] Field of Search .................. 424/305, 306; 514/531

[56] References Cited

U.S. PATENT DOCUMENTS 4,252,820 2/1981 Lantzsch ............................ 424/304
4,332,815 6/1982 Engel .................................. 424/275

FOREIGN PATENT DOCUMENTS 0031199 7/1981 European Pat. Off. .
0010879 4/1983 European Pat. Off. ............ 424/305

*Primary Examiner*—Allen J. Robinson
*Attorney, Agent, or Firm*—Harrison H. Young, Jr.; H. Robinson Ertelt; Robert L. Andersen

[57] ABSTRACT

A method for controlling soil-borne insects such as southern corn rootworm is disclosed and exemplified in which the pyrethroid 2,4,6-trifluorophenylmethyl 3-(2-chloro-3,3,3-trifluoro-1-propenyl)-2,2-dimethylcyclopropanecarboxylate is applied to the soil for initial and residual insect control.

3 Claims, No Drawings

METHOD FOR CONTROL OF SOIL-BORNE INSECTS

This invention pertains to the general field of insecticides, and relates particularly to a method for controlling soil-borne insects such as southern corn rootworm by applying to the soil certain fluorinated phenylmethyl esters of 3-(2-chloro-3,3,3-trifluoro-1-propenyl)-2,2-dimethylcyclopropanecarboxylic acid.

U.S. Pat. No. 4,332,815 discloses a broad class of perhaloalkylvinylcyclopropanecarboxylates described as having excellent insecticidal activity against Lepidoptera and Homoptera. The patent illustrates that these compounds have superior contact and foliar activity, but is silent as to any activity these compounds may have against soil-borne insects. While synthetic pyrethroids have in general shown high initial activity against soil-borne insects, they generally do not have sufficient residual activity to make them useful as soil insecticides.

It has now been found that 2,4,6-trifluorophenylmethyl cis-3-(2-chloro-3,3,3-trifluoro-1-propenyl)-2,2-dimethylcyclopropanecarboxylate, a compound encompassed by the claims in U.S. Pat. No. 4,332,815, but not specifically disclosed therein, exhibits surprising residual activity against soil-borne insects such as southern corn rootworm (*Diabrotica undecimpunctata howardi*).

In accordance with the foregoing, this invention provides a method for controlling soil-borne insects which comprises applying to the soil in which plants are or are about to be planted from about 0.4 to about 8 parts by weight of the compound 2,4,6-trifluorophenylmethyl 3-(2-chloro-3,3,3-trifluoro-1-propenyl)-2,2-dimethylcyclopropanecarboxylate per million parts by weight of soil.

This compound has the general structure shown in formula I.

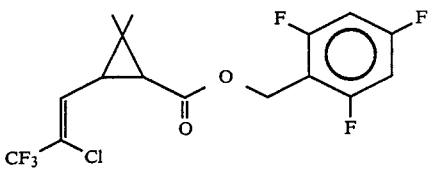

The compounds employed in this invention and certain intermediates therefor exist as cis and trans geometrical isomers, the carboxy and the substituted vinyl groups at the 1- and 3-positions of the cyclopropane ring are either cis or trans with respect to each other. Preparation of such compounds will usually yield a mixture of cis and trans isomers, designated cis,trans, in which the ratio of cis to trans may vary over a wide range.

Since positions 1 and 3 of the cyclopropane ring are asymmetric carbon atoms, there are also 4 optical isomers which may be designated 1R, cis; 1S, cis; 1R, trans; and 1S, trans.

The compounds of this invention may also exist as E or Z isomers or as mixtures of E and Z isomers, designated E, Z, depending on the spatial relationship of substituents on the α-carbon of the vinyl group to those on the β-carbon of the vinyl group.

In the cyclopropanecarboxylate art it is known there may be substantial differences in the level of insecticidal activity between the cis and trans isomers. As between the cis and trans isomer of a given synthetic cyclopropanecarboxylate, the cis isomer is often, though not always, more active than the trans and also more active than the cis,trans mixture. Similar differences in activity may also occur with respect to the E and Z isomers.

Unless a contrary intent is expressed, the invention embodies and includes all compounds in which the carboxy and substituted vinyl groups at the 1- and 3-positions of the cyclopropane ring are cis or trans, or a mixture of cis and trans configuration with respect to each other; the cis isomers, particularly the 1R,cis isomers are generally preferred. Similarly, the individual E and Z isomers, as well as the mixtures, are also contemplated by and within the scope of the present invention. The enantiomers of these isomers are also included within the scope of the invention.

The compounds may be prepared by various methods known to those skilled in the art including those described in U.S. Pat. No. 4,332,815, incorporated herein by reference. A convenient method for preparing the compounds is from a compound of formula II

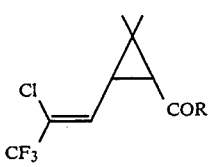

in which R is hydroxy, lower alkoxy, or halogen, by reaction with a compound containing 2,4,6-trifluorobenzyl alcohol residue, for example, by reaction with the alcohol itself when II is the acid chloride.

The examples which follow illustrate preparation of the alcohol and of I. All temperatures are in degrees Celsius, and reduced pressures are those produced by a water aspirator, unless otherwise specified.

EXAMPLE 1

Synthesis of 2,4,6-Trifluorophenylmethyl Alcohol

Step A

Synthesis of 2,4,6-Trifluorobenzoic Acid as an Intermediate

A stirred solution of 10.0 grams (0.076 mole) of 1,3,5-trifluorobenzene in 150 ml of anhydrous tetrahydrofuran, under an argon atmosphere, was cooled to −78° and 4.8 grams (0.076 mole) of n-butyllithium (as 48.7 ml of a 1.55 molar solution in hexane) was added dropwise during a 30-minute period. Upon completion of addition the reaction mixture was stirred at −78° for eight hours. A quantity of fresh, crushed dry ice, sufficient to cause the reaction mixture to become a thick slurry, was added to the reaction vessel. The reaction mixture was allowed to warm to ambient temperature as it was stirred for 26 hours. The tetrahydrofuran was removed from the reaction mixture under reduced pressure. The residue was washed into a separatory funnel with 100 ml of aqueous 2N sodium hydroxide and 200 ml of diethyl ether. The aqueous base layer was separated and the organic layer extracted with two 100 ml portions of aqueous 2N sodium hydroxide. The organic layer was discarded and the combined aqueous base layer and extracts were washed with 100 ml of diethyl ether, cooled, and acidified with concentrated hydrochloric acid. The mixture was saturated with sodium chloride and extracted with three portions of 150 ml each of diethyl ether. The combined ether extracts were dried with magnesium sulfate and filtered. The filtrate was concentrated under reduced pressure to a solid residue. The residue was recrystallized from toluene to give 10.2 grams of 2,4,6-trifluorobenzoic acid; mp 225°–227°.

The nmr spectrum was consistent with the assigned structure.

Analysis calc'd for $C_7H_3F_3O_2$: C 47.75; H 1.72; Found: C 47.68; H 1.42.

Step B

Synthesis of 2,4,6-Trifluorophenylmethyl Alcohol

To a stirred solution of 4.1 grams (0.023 mole) of 2,4,6-trifluorobenzoic acid in 50 ml of anhydrous tetrahydrofuran, under a nitrogen atmosphere was added dropwise 4.0 grams (0.047 mole) of borane-tetrahydrofuran complex (as 46.6 ml of a 1.0 molar solution in tetrahydrofuran). The addition caused the reaction mixture to foam. Upon completion of addition the reaction mixture was stirred at ambient temperature for two hours, then was heated under reflux for one hour. The reaction mixture was cooled and 50 ml of water was cautiously added. The tetrahydrofuran was removed under reduced pressure and the residue washed into a separatory funnel with 100 ml of aqueous 2N sodium hydroxide. The mixture was extracted with three 100 ml portions of methylene chloride. The combined extracts were dried with magnesium sulfate and filtered. The filtrate was concentrated under reduced pressure to give 3.2 grams of 2,4,6-trifluorophenylmethyl alcohol as an oil.

The nmr spectrum was consistent with the assigned structure.

EXAMPLE 2

Synthesis of 2,4,6-Trifluorophenylmethyl cis-3-(2-chloro-3,3,3-trifluoro-1-propenyl)-2,2-dimethylcyclopropanecarboxylate A stirred solution of 1.5 grams (0.009 mole) of 2,4,6-trifluorophenylmethyl alcohol and 0.8 gram (0.01 mole) of pyridine in 30 ml of toluene was warmed to 50° and 2.4 grams (0.009 mole) of cis-3-(2-chloro-3,3,3-trifluoro-1-propenyl)-2,2-dimethylcyclopropanecarbonyl chloride was added. The addition caused a solid precipitate to form in the reaction mixture. Upon completion of the addition of the carbonyl chloride, the reaction mixture was heated under reflux for two hours, then allowed to cool to ambient temperature as it was stirred for 16 hours. The reaction mixture was placed on a column of 100 grams of silica gel and eluted with toluene. The appropriate fractions were combined and concentrated under reduced pressure to a clear residual oil. The residual oil was distilled under reduced pressure using a Kugelrohr distilling system. The appropriate fractions were combined to give 0.4 gram of 2,4,6-trifluorophenylmethyl cis-3-(2-chloro-3,3,3-trifluoro-1-propenyl)-2,2-dimethylcyclopropanecarboxylate as an oil; $n_D^{25}$ 1.4681.

The nmr spectrum was consistent with the assigned structure: $\delta(CDCl_3, TMS)$ 1.46 (s, 6H), 1.87–2.33 (m, 2H), 5.17–5.27 (m, 2H), 6.50–7.03 (m, 3H).

Analysis calc'd for $C_{16}H_{13}ClF_6O_2$: C 49.69; H 3.39 Found: C 50.23; H 3.33.

In the method of this invention the active compound is applied by incorporating a formulation thereof into the soil in which agricultural crops have been or will be planted, that is, the locus of infestation. This may be achieved by broadcasting the formulation over the planted area or the area to be planted or by banding the application in the root zone where plants have been or are to be planted. It will be readily apparent where the latter method is employed that an amount of formulation sufficient to supply an insecticidally effective concentration of active ingredient in the soil must be applied to the root zone. A suitable concentration for this purpose is in the range of 0.4 to about 8 parts by weight of the active ingredient per million parts of soil. This would be equivalent to 0.16 Kg/ha to 3.2 Kg/ha of active ingredient for banded application or 0.8 to 16 Kg/ha for broadcast application.

Typical formulations for use in the method of the invention include the active ingredient in combination with an agriculturally acceptable carrier or extender, preferably with a surface active agent, and optionally with other active ingredients. Suitable formulations include granules of various sizes, dusts, wettable powders, emulsifiable concentrates, solutions, dispersions, and the like, with the choice depending upon the environmental factors at the situs of infestation and the method of application selected. A typical formulation may vary widely in concentration of the active ingredient depending upon the additives and carriers used and the desired mode of application. Thus active ingredient may be present at a concentration of 0.1% to 99.5% by weight of the formulation. An agriculturally acceptable carrier may comprise about 99.5% by weight to as low as 0.5% by weight of the formulation. Compatible surface active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredient. The concentration of the active ingredient in use dilution may be in the range of about 0.01 to about 10% by weight.

The compound of Example 2 was incorporated in soil and tested for initial and residual activity against third instar southern corn rootworm larvae by the general method of G. R. Sutter, J. Econ. Entom., Vol 75(3), 489-91 (1982), incorporated herein by reference, except that in residual tests the soil was infested twenty-eight days after treatment with the active ingredient. Test methods are described in Example 3.

EXAMPLE 3

Tests for Biological Activity

Initial Evaluation

A stock solution of the test compound was prepared by dissolving 4.8 mg in 10 ml of acetone and diluting with 90 ml of acetone/water (1:9). The addition of 5 ml of this stock solution to 30 g of air-dried, clay loam soil in a 3-oz plastic cup provided a concentration of 8 ppm of the test compound in the soil. Serial dilution of the stock solution was used to obtain concentrations of the test compound in soil of 4, 2, 1, 0.5, 0.25, 0.125, and 0.0625 ppm. In all cases 5 ml of a solution having the required concentration was added to 30 g of soil. The treated soil was allowed to stand uncovered in a hood for 0.5 hour to evaporate the acetone. Before infesting the soil with southern corn rootworm larvae, the soil was mixed thoroughly. Two three-day-old corn sprouts and ten early third-stage (9–10 days old) southern corn rootworm larvae were placed in the cup which was then covered with a plastic lid, and held in a closed plastic bag. After storage at 74°–78° F. for 48 hours, the mortality of the larvae was determined by removing the cup from the plastic bag, removing the cover, and placing the contents of each cup in a modified Berlese polyethylene funnel fitted with an 18-mesh screen. The funnels were placed over containers of an aqueous detergent solution. Incandescent lights (100 watts) were placed 36 cm above the soil samples. The heat from these lights slowly dried the soil which caused larvae that had not been affected by the test compound to emerge from the soil and drop into the detergent solution. The percent mortality was determined in this manner for each concentration. Duplicate tests were run at each concentration.

Residual Assay

The residual activity of the test compounds was determined in the same manner as the initial evaluation except that treated soil was not infested with larvae until 28 days after treatment. Corn sprouts were placed in each cup and mixed with treated soil immediately before larvae were placed in the soil. Concentrations of test compounds were 8, 4, 2, and 1 ppm.

Results of the tests recorded in Table I show that the high initial level of activity against southern corn rootworm is diminished only moderately 28 days after application to soil, thereby demonstrating surprising residual activity for the active ingredients of the present invention.

TABLE I

Insecticidal Activity of 2,4,6-Trifluorophenylmethyl cis-3-(2-chloro-3,3,3-trifluoro-1-propenyl)-2,2-dimethylcyclopropanecarboxylate in the Soil Against the Southern Corn Rootworm

| Rate of Application | Percent Kill | $LC_{50}$ |
|---|---|---|
| Initial Activity | | |
| 4.0 ppm | 100 | |
| 2.0 | 85 | |
| 1.0 | 85 | |
| 0.5 | 70 | |
| 0.25 | 25 | 0.4 ppm |
| Residual Activity - 28 Day | | |
| 8.0 ppm | 100 | |
| 4.0 | 90 | |
| 2.0 | 70 | |
| 1.0 | 50 | |

I claim:
1. A method for controlling soil-borne insects of the genus Diabrotica which comprises applying to the soil in which plants are or are to be planted an insecticidally effective amount of 2,4,6-trifluorophenylmethyl-3-(2-chloro-3,3,3-trifluoro-1-propenyl)-2,2-dimethylcyclopropanecarboxylate.

2. The method of claim 1 in which there, is employed the cis or 1R,cis isomers of active ingredient or mixtures thereof.

3. The method of claim 1 in which there is employed a quantity of active ingredient sufficient to supply a concentration in the soil of the root zone equivalent to 0.4 to 8 parts by weight per million parts by weight of soil.

* * * * *